United States Patent [19]

Tichy

[11] Patent Number: 5,002,487
[45] Date of Patent: Mar. 26, 1991

[54] PERIODONTIC TOOL WITH TRIANGULAR VIBRATION PATH

[76] Inventor: Edward Tichy, Number 21, Rte. 132, Woodbury, Conn. 06798

[21] Appl. No.: 307,408

[22] Filed: Feb. 7, 1989

[51] Int. Cl.$^5$ .............................................. A61O 1/07
[52] U.S. Cl. ................................... 433/122; 433/118; 128/62 A
[58] Field of Search .............. 433/118, 122, 125, 131; 128/62 A, 36, 37

[56] References Cited

U.S. PATENT DOCUMENTS

| Re. 31,603 | 6/1984 | Christensen | 128/33 |
| 3,159,859 | 12/1964 | Rasmussen | 128/62 A |
| 3,466,689 | 9/1969 | Aurelio et al. | 128/62 A |
| 3,552,022 | 1/1971 | Axelsson | 433/122 |
| 3,563,233 | 2/1971 | Bodine | 128/62 A |
| 3,919,575 | 11/1975 | Weber et al. | 128/36 X |
| 3,967,617 | 7/1976 | Krolik | 128/62 A |
| 4,173,828 | 11/1979 | Lustig et al. | 433/122 X |

Primary Examiner—Robert P. Swiatek
Assistant Examiner—Nicholas A. Lucchesi
Attorney, Agent, or Firm—Chilton, Alix & Van Kirk

[57] ABSTRACT

The tool has an elongated, at least partly hollow body including a handle portion and a free end adapted for carrying a periodontic end effector. A shaft, powered by a motor and rechargeable battery, rotates within the hollow portion. A fixed ring is mounted transversely in the hollow portion of the body, and a gear member is rotated by the shaft along the ring. An eccentric weight is carried by the gear member and is displaced so that the center of gravity of the eccentric weight follows a substantially triangular path as the gear member moves through one cycle. This vibrates the tool, and the end effector, in a substantially triangular path which achieves advantages in cleaning the tooth proximal surfaces by closely following the shape of the embrasure.

15 Claims, 4 Drawing Sheets

PERIODONTIC TOOL WITH TRIANGULAR VIBRATION PATH

BACKGROUND OF THE INVENTION

The present invention relates to hand-held periodontic tools, and more particularly, to apparatus for imparting a vibratory motion to the end effector carried by such tool.

A variety of hand-held, vibrating periodontic tools are known in the art. These are driven either electrically or by a mechanical action, such as a wound spring. The shape and manner of mounting the end effectors to the housing or body, and the vibration path followed by the end effector, take many forms.

This variety in the manner of connecting and driving the end effector has resulted in five basic paths of tip movement. These include linear reciprocation either laterally to the tip (such as brush scrubbing action) or along the tip axis (such as a hammer action). Various complete or partial rotary paths have also been used, including circular, oval, or fan-shape, with the imaginary planes defined by these paths, being oriented either parallel or perpendicularly to the tip axis.

Although these various motions have relative advantages and disadvantages, none is optimized for cleaning the proximal, interdental surfaces where, for example, plaque is likely to accumulate.

SUMMARY OF THE INVENTION

It is thus an object of the present invention to provide a hand-held periodontic tool and a drive system therefor, which provides a new path of motion for the end effector, or tip, carried at the free end of the tool.

It is a particular object of the invention to impart a travel path to the end effector that more closely conforms with the interdental proximal surfaces, i.e., the shape of the embrasure.

It is a more particular object of the present invention to impart a substantially triangular vibration path to the end effector.

These objects are accomplished by a hand-held periodontic tool including an elongated, substantially tubular handle. An elongated shank extends from the handle and has a free end remote from the handle. A resilient tip is carried by the shank free end, and a drive system is carried within the handle for imparting a substantially triangular path of movement to the tip.

Preferably, the hand-held periodontic tool comprises an elongated, at least partly hollow body having a handle portion and a free end adapted for carrying a periodontic end effector. A shaft is powered to rotate within the hollow portion of the body. A gear member is located in the hollow portion and driven by the shaft. The gear member is constrained to move periodically along a prescribed path that is generally transverse to the longitudinal direction of the body. An eccentric weight is carried by the gear member, such that the center of gravity of the weight follows a substantially triangular path as the gear member moves through one cycle of the periodic motion. In this manner, the tool including the end effector is vibrated by the momentum of the center of gravity of the eccentric weight, in a substantially triangular pattern.

The preferred drive system includes a powered, rotating shaft on the axis of the tool, and a circular track ring held in stationary, coaxial position along the inner wall of the tool. A gear member in the form of a travel wheel is operatively associated between the shaft and the track for traversing a circular path defined by the track. An eccentric drive weight is carried by the travel wheel and has a center of gravity radially offset from the tool axis and the travel wheel axis. As the shaft is rotated, the gear interacts with the circular track such that the drive weight follows a substantially triangular path within the track, thereby imparting the desired triangular vibratory motion to the tool body, shank, and tip.

BRIEF DESCRIPTION OF THE DRAWINGS

These and other objects and advantages of the invention will be described below with reference to the accompanying drawings, in which.

DESCRIPTION OF THE PREFERRED EMBODIMENT

Figure 1:
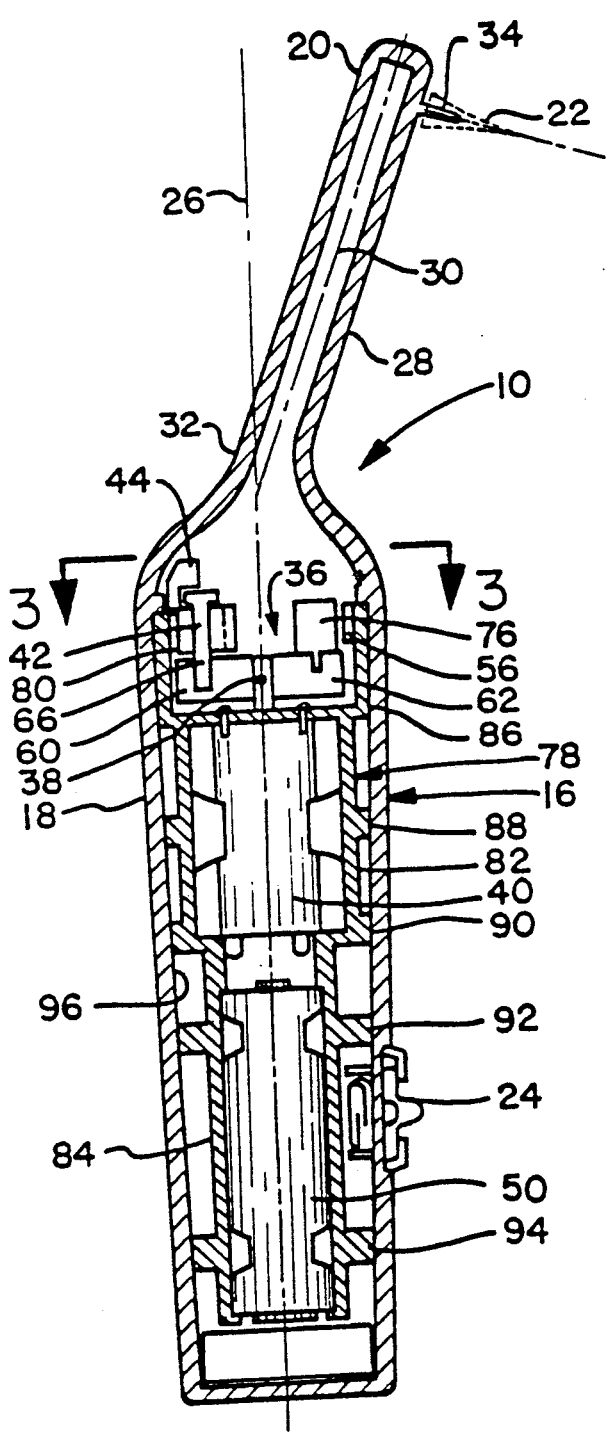
FIG. 1 is a front elevation view of the preferred embodiment of the periodontic tool and its associated electrical charging stand.

FIG. 1 shows a hand-held periodontic tool in a position either partly inserted, or partly removed, from an associated charging base unit 12 which is connected through wires 14 to an electrical outlet or the like (not shown). The base unit 12 is conventional and forms no part of the present invention. The tool 10 is in the form of an elongated body 16 which is at least partly hollow and has a handle portion 18 and a free end 20 adapted for carrying a periodontic end effector, or tip 22. Typically, an on-off switch 24 is associated with the handle portion 18 for initiating or terminating the vibratory action of the tip 22.

FIGS. 2-6 illustrate the preferred construction and operation of the tool in accordance with the invention. The tubular handle portion 18 is elongated and has a longitudinal axis 26 extending therethrough. An elongated shank 28 extends from the handle and has a free end 20 remote from the handle 18. Preferably, the shank 28 is an integral extension of the handle portion and has a shank axis 30 which intersects the handle axis 26 substantially at the transition 32 between the handle and the shank.

Tip 22 is mounted at the free 20 end of the shank 28, preferably oriented so that the tip axis 34 is substantially perpendicular to the shank axis 30. Although a variety of tips 22 may be employed with the invention, the preferred tip is a modified cone, that resembles a spire, and, preferably, is ribbed or fluted. This and other tips which may be employed with the invention are described in copending U.S. Pat. application Ser. No. 241,011, filed Sept. 1, 1988 and entitled "Hand-Held Periodontic Tool", the disclosure of which is hereby incorporated by reference.

In accordance with the invention, the tool 10 is vibrated so that the tip 22 is driven along a substantially triangular path of movement. This is accomplished by the use of a drive system 36, preferably within the handle tubular portion, which imparts a force to the walls of the handle that is substantially triangular as viewed transversely to the axis of the handle 18.

The drive system 36 includes a shaft 38 powered by an electric motor 40 for rotation about the axis 26. A gear member 42 in the hollow portion of the handle is translated by the shaft 38 and constrained to move periodically along a prescribed path that is generally transverse to the longitudinal direction or axis 26 of the body 16. The gear member 42 carries an eccentric drive weight 44, which has a center of gravity 46 that follows a substantially triangular path 48 as the gear member 42 moves through one cycle of its periodic movement. Thus, the tool 10 including the end effector 22 is vibrated by the momentum of the center of gravity 46 of the eccentric drive weight 44.

In a somewhat conventional fashion, the shaft 38 can be rotated by an associated motor 40 which, in turn, is electrically connected to a rechargeable battery 50. Preferably, the battery 50 is rechargeable through a magnetic pack 52 which interacts with the active member 54 of the charging base unit 12 when the tool is inserted therein (FIG. 1).

The complete drive system 36 preferably is formed by a fixed ring 56 mounted coaxially within the handle 18, having internally directed teeth 58. A drive arm 60 extends radially from the shaft 38 for rotation therewith. Preferably, the drive arm 60 extends below the ring 56 and is integral with balance arm 62 so that together they form a support bar or arm extending substantially diametrically under the ring. The drive arm 60 carries a gear member in the form of a circular, externally toothed travel wheel 42 which rotates about an axis 64 defined by a pin 66 or the like which secures the gear to the arm 60. The gear or wheel 42 has a diameter less than the radius of the ring 56 and the teeth 68 on the wheel 42 are sized to engage the teeth 58 of the ring and produce rotation of the wheel 42 relative to the wheel axis 64, as the drive arm 60 rotates about axis 26.

Figure 6:
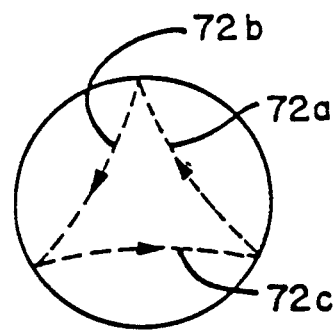
FIG. 6 is a diagrammatic representation of the preferred triangular path of the center of gravity of the eccentric weight, wherein each leg of the triangle is somewhat curved.

An eccentric mass 44 is affixed to the travel wheel 42, preferably such that the center of gravity 46 of the eccentric mass is located at the radially outer extent of the wheel 42. The path of movement traced by the center of gravity 46 of the eccentric mass is shown schematically by the circles 70 in FIG. 4, as a consequence of the rotation of the drive arm 60. It can be seen that the center of gravity 46 travels along an equilateral triangle 48 that is circumscribed by the fixed ring 56. The effective size of the equilateral triangle, i.e., the length of each leg 72 between apexes 74, is defined by the radial position of the center of gravity 46 of the eccentric mass 44 relative to the shaft axis 26, whereas the shape of the path of the center of gravity 46 along each leg 72 between apexes 74, is defined by the radius of the travel wheel 42. As shown in FIG. 6, the preferred path along each leg 72a,b,c of the triangle 74 is somewhat concave.

Figure 2:
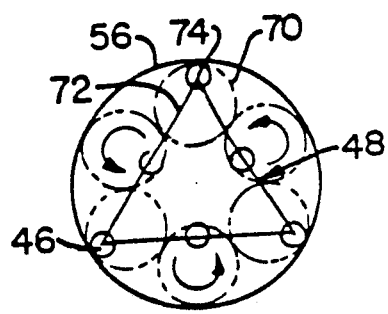
FIG. 2 is a side elevation view in section, showing the drive system in accordance with the preferred embodiment of the invention.
Figure 3:
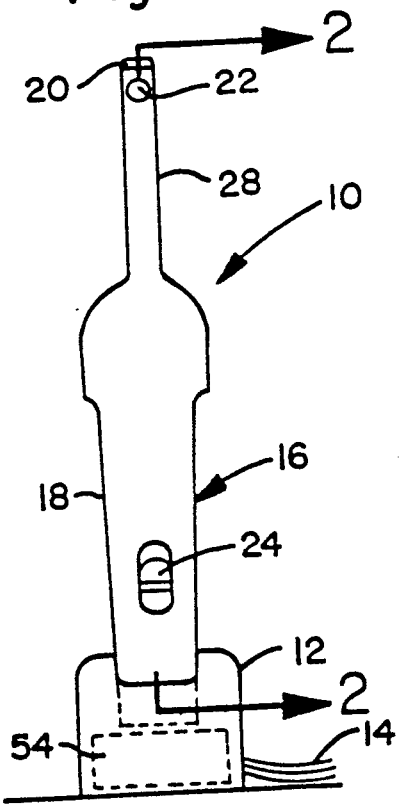
FIG. 3 is a cross-section view taken along lines 3-3 of FIG. 2.
Figure 4:
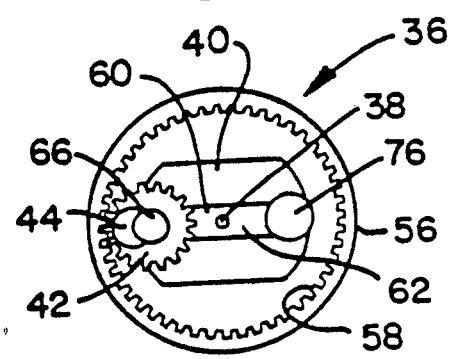
FIG. 4 is a diagrammatic representation of the triangular path followed by the center of gravity of the eccentric weight in accordance with the invention.
Figure 5:
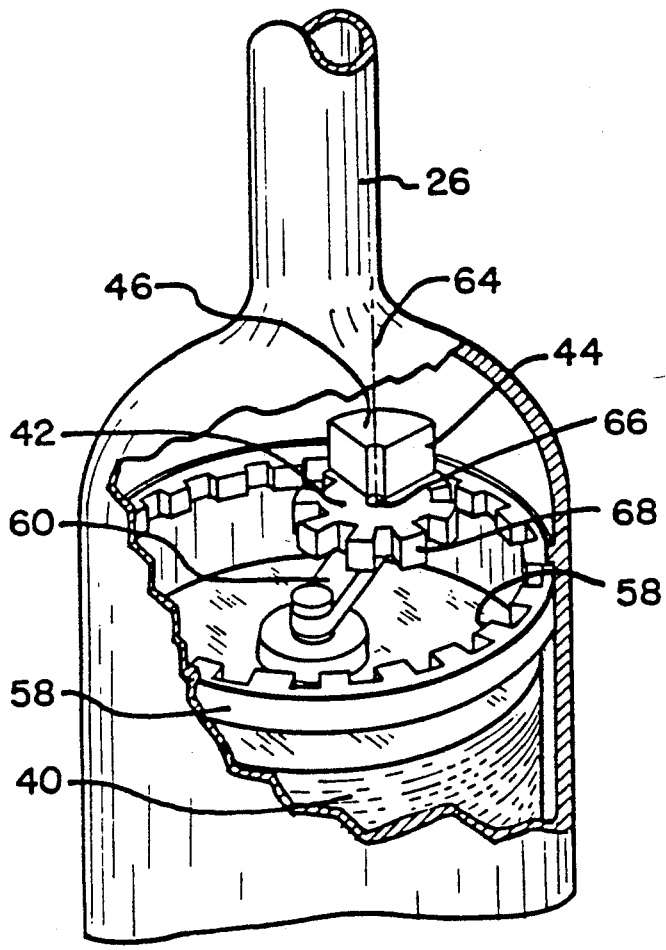
FIG. 5 is a perspective view, partially cut away, of the portion of the tool containing the drive system components that impart the triangular vibration force to the tool.

The portion of the support arm 62 extending opposite the drive arm 60 has been omitted in FIG. 5 for clarity, but is visible in FIG. 2. This portion 62 of the support arm can be characterized as a balance arm, which carries a counter balance weight 76. Preferably, if the shaft 38 is viewed as a fulcrum and the diametral support bar 60,62 as a lever, the moment associated with the balance arm 62 and the associated counter balance weight 76, is equal to the moment associated with the drive arm 60 and the travel wheel 42 and associated spline pin 66. Thus, the vibrating force is produced substantially entirely by the triangular path 48 of movement of the center of gravity 46 of the eccentric mass 44.

The preferred way of securing the drive system 36 within the handle 18 is shown in FIG. 2. A harness 78 having three main sections envelopes the drive system 36 and is, in turn, enveloped by the tubular handle 18. The harness 78 has an upper section 80 containing the exposed shaft 38, the support arm 60,62, the travel wheel 42, and eccentric mass 44. The fixed ring 56 is preferably also attached to the upper section 80 of the harness 78, but could, alternatively, be attached directly to the inner wall of handle 18.

The center section 82 of the harness 78 contains the motor 40, and the lower section of the harness 78 contains the battery 50. The outer extremities 86,88,90,92,94 of the harness define an imaginary surface which substantially exactly conforms to the inner surface 96 of the handle 18. Thus, the harness 78 is assembled with the drive system 36 components enveloped therein, and is placed in a half-section of the body 16, as shown in FIG. 2. Thereafter, the other half-section of the body is placed over the first half-section and joined thereto, forming the completed body as shown in FIG. 1. The radially outer portions of the harness thus come into and remain in contact with respective inner surfaces 96 of the handle and are essentially rigidly maintained therein through friction at the plurality of contact areas.

Preferably, the tubular portion of the body 16 containing the eccentric weight 44 is located at the upper end of the handle 18, near the transition 32 to the shank portion 28 of the tool 10.

Figure 7:
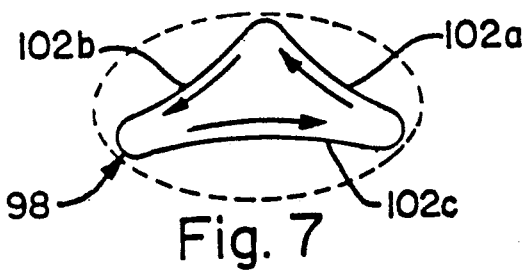
FIG. 7 is a diagrammatic representation of the path of the movement of the tip portion of the tool associated with FIG. 6.
Figure 8:
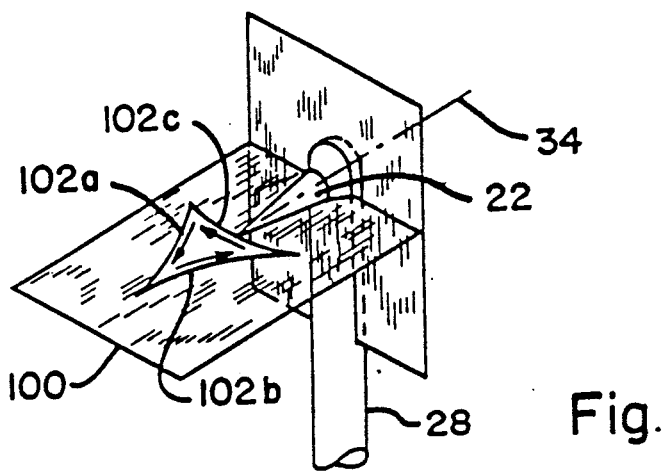
FIG. 8 is a diagrammatic representation of the triangular path of movement of the tip in accordance with the invention.

FIGS. 7-10 show the path of tip movement achieved with the present invention, and present a comparison with conventional tip movements. As shown in FIGS. 7 and 8, the triangular path 98 of the tip 22 is substantially confined to a plane 100 that is parallel to, and contains, the tip axis 34 and is transverse to the axis of shank 28.

As viewed from the tip, the path has a base leg 102c, a right leg 102a, and a left leg 102b. It should be appreciated that when the tool 10 is viewed from above the shank 28, each of the apexes of the triangular path shown in FIG. 8 will point in substantially the same direction as one of the apexes 74 of the path of the center of gravity 46, shown in FIG. 4.

Figure 9:
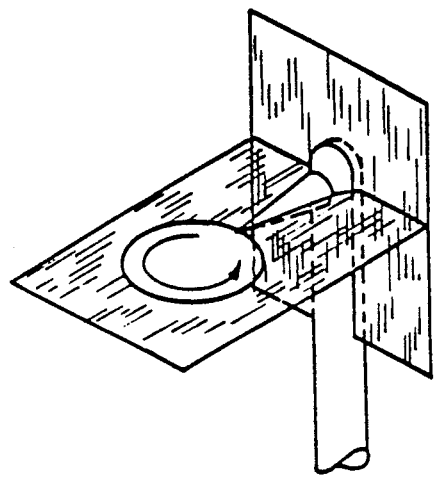
FIG. 9 is a diagrammatic representation of a typical concentric or circular tip motion known in the prior art.
Figure 10:
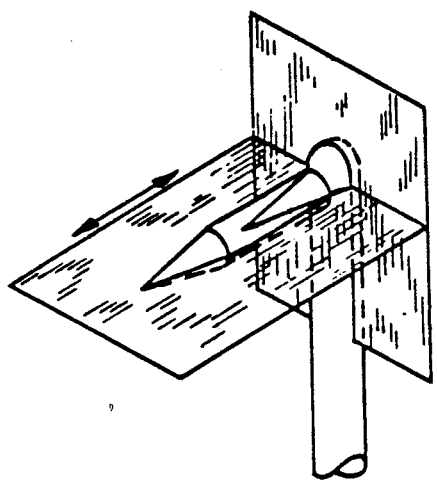
FIG. 10 is a diagrammatic representation of a typical reciprocating tip motion as known in the prior art.

Prior art paths are shown in FIGS. 9 and 10, which, although generally also confined to a single plane, do not produce the triangular path achieved with the present invention.

Figure 11:
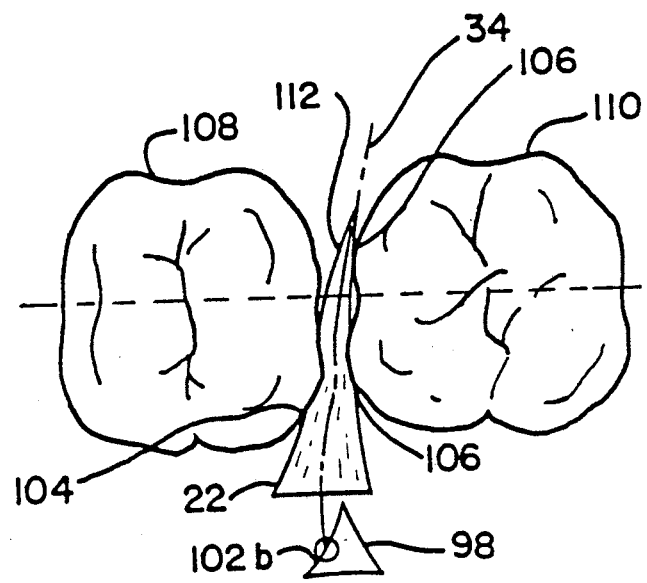
FIG. 11 is a diagrammatic representation of the relationship of the tip to the user's teeth when the vibratory position of the tip is associated with the left leg of the triangle.
Figure 12:
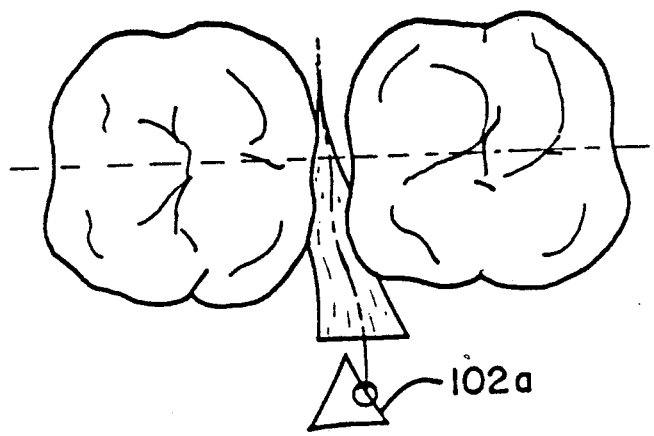
FIG. 12 is a diagrammatic representation of the relationship of the tip to the user's teeth when the vibratory position of the tip is associated with the right leg of the triangle.
Figure 13:
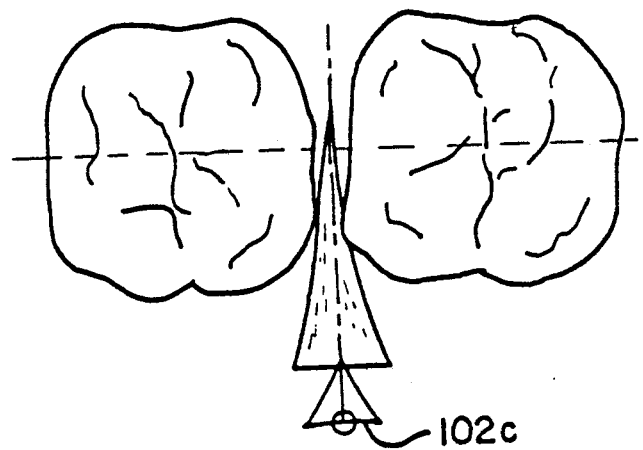
FIG. 13 is a diagrammatic representation of the relationship of the tip to the user's teeth when the vibratory position of the tip is associated with the base leg of the triangle.

FIGS. 11-13 illustrate how the triangular drive path 98 of the tip 22 improves the performance characteristics for periodontal effectiveness. In FIG. 11, the tip 22 is shown in a position corresponding to the middle of the left leg 102b of the triangle 98. The resulting deformation of the soft tip 22 produces firm contact against the proximal surfaces 104,106 between two teeth 108,110, first on one tooth 108 as it enters the embrasure 112 as shown in FIG. 11, then against the adjacent tooth 110 as it pulls out of the embrasure. FIG. 12 represents the withdrawing tip position corresponding to the center of the right leg 102b of triangle 98. The deflection and momentary bending of the tip 22 along its axis 34 promotes maximum contact of the tip 22 with the teeth.

With the preferred tip 22 as shown, the flexibility of the tip promotes conforming of the tip material to the tooth surfaces. The triangular drive path 98 conforms closely to the shape of the embrasure 112 and allows the tip to travel smoothly along the proximal surfaces 104,106. The portion of the tip movement cycle shown in FIG. 13, in which the tip 22 repositions itself along base leg 102c but provides the minimum cleaning during the cycle, is relatively small as compared with the portions of the cycle shown in the prior art, FIGS. 9 and 10, where cleaning is nonexistent or minimal.

It should be appreciated that the preferred embodiment of the invention has been described herein, but that other forms and variations will fall within the scope of the appended claims.

I claim:

1. A hand held periodontic tool comprising:
 a body having an elongated handle extending along a first axis and a shank extending along a second axis which intersects with the first axis, the shank having a free end;
 a dental tip carried by the free end and extending transversely to the second axis; and
 drive means carried within the body, for imparting a substantially triangular path of movement to the tip, wherein said triangular path lies substantially in a plane that is oblique to the first axis.

2. A hand held periodontic tool comprising:
 a body having an elongated handle and a free end;
 a dental tip carried by the free end; and
 drive means located within the handle, for imparting a substantially triangular path of movement to the tip, said drive means including a drive weight having a center of gravity and means for displacing the center of gravity of the drive weight along a substantially triangular, planar path oriented transversely to the handle.

3. The periodontic tool of claim 2, wherein the means for displacing the center of gravity includes,
 a circular, internally toothed stationary ring mounted within the handle,
 a circular gear having a gear rotation axis and external teeth engaging the ring, the gear having a diameter less than the radius of the ring, said drive weight being mounted on the gear offset from the gear axis; and
 means for advancing the gear along the ring, whereby the center of gravity of the drive weight is displaced along a triangular path that is circumscribed by the ring.

4. The periodontic tool of claim 3, wherein the drive means further include,
 an electric motor having a rotating shaft oriented longitudinally with the handle,
 a support arm rigidly extending transversely to the shaft, and
 means for mounting the circular gear on the support arm, whereby the circular gear rotates about the gear axis as the gear follows the stationary ring.

5. The periodontic tool of claim 4, wherein the drive means further includes a counter weight carried by the support arm, for counter balancing the weight of the support arm and gear.

6. The periodontic tool of claim 3, wherein the center of gravity of the drive weight is located substantially at the radially outer extent of the circular gear.

7. The periodontic tool of claim 2, wherein the body includes a shank projecting from the handle and carrying said tip, and wherein the drive means is located adjacent the shank.

8. The periodontic tool of claim 2, further including a harness which closely envelopes the drive means and is closely enveloped by the handle.

9. A hand held periodontic tool comprising:
 an elongated, at least partly hollow body having a handle portion and a free end adapted for carrying a periodontic end effector;
 a shaft powered to rotate within the hollow portion;
 a wheel member located in the hollow portion and driven by the shaft, the wheel member being constrained to move cyclicly along a prescribed path that is generally transverse to the longitudinal direction of the body;
 an eccentric weight carried by the wheel member, the eccentric weight having a center of gravity that follows a substantially triangular path as the wheel member moves through one cycle along the path;
 whereby the tool including end effector is vibrated by the momentum of the center of gravity of the eccentric weight.

10. The periodontic tool of claim 9, wherein said prescribed path is defined by a track situated between the wheel member and the inner surface of said hollow portion.

11. In combination with a hand held periodontic tool having an axis, a drive system for vibrating the tool, comprising:
 a means for rotating a shaft on the axis;
 a circular track ring held in a stationary, coaxial position within the tool;
 gear means operatively associated between the shaft and the track ring, for periodically traversing a path defined by the ring; and
 a drive weight carried by the gear means and having a center of gravity radially offset from the tool axis, said center of gravity following a substantially triangular path within the ring, as said shaft rotates.

12. The drive system of claim 11, wherein the gear means includes a circular travel gear having a gear rotation axis and circumferentially engaging the track ring, the travel gear having a diameter smaller than the radius of the ring, said drive weight being mounted on the gear in offset relation from the gear axis.

13. The drive system of claim 12, wherein the gear means includes,
   a support arm rigidly extending transversely to the shaft, and
   means for mounting the travel gear on the support arm for rotation about the gear axis.

14. The drive system of claim 13, including a counter weight in rigid relationship with the support arm, for counter balancing the weight of the support arm, travel gear and the means for mounting the gear.

15. The drive system of claim 11, wherein the center of gravity of the drive weight is located substantially at the radially outer extent of the travel gear.

* * * * *